(12) United States Patent
Shim

(10) Patent No.: US 10,658,085 B2
(45) Date of Patent: May 19, 2020

(54) METHOD FOR DETERMINING PATIENT-SPECIFIC BLOOD VESSEL INFORMATION

(71) Applicant: KNU-INDUSTRY COOPERATION FOUNDATION, Chuncheon-si, Gangwon-do (KR)

(72) Inventor: Eun Bo Shim, Chuncheon-si (KR)

(73) Assignee: KNU-INDUSTRY COORPORATION FOUNDATION, Chuncheon-si, Gangwon-do (KR)

( * ) Notice: Subject to any disclaimer, the term of this patent is extended or adjusted under 35 U.S.C. 154(b) by 294 days.

(21) Appl. No.: 15/506,909

(22) PCT Filed: Aug. 31, 2015

(86) PCT No.: PCT/IB2015/001476
§ 371 (c)(1),
(2) Date: Feb. 27, 2017

(87) PCT Pub. No.: WO2016/030744
PCT Pub. Date: Mar. 3, 2016

(65) Prior Publication Data
US 2017/0286628 A1    Oct. 5, 2017

(30) Foreign Application Priority Data
Aug. 29, 2014    (KR) .......................... 10-2014-0114553

(51) Int. Cl.
*G16H 50/50*    (2018.01)
*A61B 5/02*    (2006.01)
(Continued)

(52) U.S. Cl.
CPC ............... *G16H 50/50* (2018.01); *A61B 5/02* (2013.01); *A61B 5/02007* (2013.01);
(Continued)

(58) Field of Classification Search
CPC .......... G16H 50/50; A61B 5/02; A61B 6/504; A61B 6/507; A61B 6/5217; A61B 5/0044;
(Continued)

(56) References Cited

U.S. PATENT DOCUMENTS 6,501,848 B1    12/2002 Carroll et al.
9,087,147 B1 *    7/2015 Fonte ................... A61B 5/7275
(Continued)

FOREIGN PATENT DOCUMENTS

JP    2014-079649 A    5/2014
KR    10-1524955 A    6/2015
(Continued)

*Primary Examiner* — Kamini S Shah
*Assistant Examiner* — Faraj Ayoub
(74) *Attorney, Agent, or Firm* — Novick, Kim & Lee, PLLC; Jae Youn Kim

(57) ABSTRACT

The present invention relates to a method for determining patient-specific blood vessel information. More specifically, the present invention relates to a method for determining patient-specific cardiovascular information by applying a simplified coronary circulation model thereto. Furthermore, the present invention relates to a method for determining a blood flow rate for branches of a blood vessel having originated from an artery of each patient. According to the present invention, the method for determining cardiovascular information by using a computer system comprises the steps of: receiving image data including a plurality of coronary arteries having originated from the aorta; processing the image data so as to generate a three-dimensional shape model of the plurality of coronary arteries; simulating a blood flow for the generated three-dimensional shape model of the plurality of coronary arteries; and determining a fractional flow reserve (FFR) of the respective coronary arteries with the blood flow simulation result. In the blood flow simulation step for the three-dimensional shape model (Continued)

of the plurality of coronary arteries, a computational fluid dynamics model is applied to the three-dimensional shape model of the coronary arteries, and a centralized parameter model to be combined with the computational fluid dynamics model uses a simplified coronary circulation model including coronary arteries, capillaries of the coronary arteries, and coronary veins.

5 Claims, 13 Drawing Sheets

(51) Int. Cl.
*A61B 6/00* (2006.01)
*G06F 17/11* (2006.01)
(52) U.S. Cl.
CPC .............. *A61B 6/504* (2013.01); *A61B 6/507* (2013.01); *A61B 6/5217* (2013.01); *G06F 17/11* (2013.01)
(58) Field of Classification Search
CPC ...... A61B 5/02007; A61B 5/026–0295; G06F 17/11; G06F 19/00; G06Q 50/22

USPC .............................................. 703/2; 600/427
See application file for complete search history.

(56) References Cited

U.S. PATENT DOCUMENTS

| | | | |
|---|---|---|---|
| 2003/0032853 A1* | 2/2003 | Korakianitis | ....... A61M 1/1086 600/16 |
| 2012/0072190 A1 | 3/2012 | Sharma et al. | |
| 2013/0246034 A1* | 9/2013 | Sharma | .............. A61B 5/02007 703/11 |
| 2014/0148693 A1* | 5/2014 | Taylor | ................ A61B 5/02007 600/427 |

FOREIGN PATENT DOCUMENTS

| | | |
|---|---|---|
| WO | 2014/091339 A1 | 6/2014 |
| WO | 2014-111927 A1 | 7/2014 |
| WO | 2014-111929 A1 | 7/2014 |

* cited by examiner (a) normal vessel      (b) vessel with 50% diameter stenosis

METHOD FOR DETERMINING PATIENT-SPECIFIC BLOOD VESSEL INFORMATION

TECHNICAL FIELD

The present invention relates to a method for determining patient-specific blood vessel information. More specifically, the present invention relates to a method for determining patient-specific cardiovascular information using a simplified coronary circulation model. Furthermore, the present invention relates to a method for determining a blood flow rate for branches of a blood vessel having originated from an artery of each patient.

BACKGROUND ART

In general, the fractional flow reserve (FFR) is widely used as a clinical indicator for evaluating the functional severity of coronary artery stenosis. A computer simulation method based on computed tomography (CT) data of a patient is a non-invasive method for calculating the FFR. This method can provide a detailed analysis result to the hemodynamics of a stenosed coronary artery by combining a computational fluid dynamics model with a lumped parameter model of a cardiovascular system.

Pijls et al. have introduced, as an indicator of a coronary artery disease, the fractional flow reserve (FFR) which refers to a ratio of a micro-vessel having a completely expanded state and a micro-vessel having a stenosed state. Pijls et al. have showed a method of measuring the FFR using a guide wire technique, which became a technique of evaluating the degree of stenosis of a coronary artery.

Kim et al. has presented a non-invasive simulation method which takes advantage of a CT image and patient information when evaluating an FFR value. This is a method in which a computational fluid dynamics technique for hemodynamic calculation of an aorta and a coronary vessel is combined with a lumped parameter model of the whole cardiovascular system. The validity and usefulness of this simulation model has been verified through several studies (Min et al., 2012; Koo et al., 2011). However, the model developed by Kim et al. requires complex calculation and identification of many parameters, consequently increasing the uncertainty of simulation, because the aorta is included in the computational fluid dynamics model and because the whole cardiovascular system is included in the lumped parameter model.

Korean Patent No. 10-1524955 (entitled: patient-specific blood flow modeling method and system) discloses a method and system for determining cardiovascular information of a patient. The cardiovascular information determining method disclosed in the above patent includes the steps of: receiving a patient-specific data on the geometry of an anatomical structure of a patient including at least a part of a plurality of coronary arteries originating from an aorta; generating a three-dimensional model indicating a first part of the anatomical structure of the patient including at least a part of the plurality of coronary arteries based on the patient-specific data; generating a physics-based model on blood flow characteristics in the first part of the anatomical structure at least partially based on a mass or volume of myocardial tissue; and determining a fractional flow reserve in the first part of the anatomical structure based on the three-dimensional model and the physics-based model.

In the method disclosed in the above patent, the physics-based model makes use of a lumped parameter model which indicates blood flow through the boundary of the three-dimensional model. In the case of using the lumped parameter model, a blood flow rate condition is set based on the volume of a ventricular muscle. This is based on the assumption that the blood flow rate grows larger in a region having a larger volume of a ventricular muscle among the regions to which blood is supplied by coronary arteries. In the method disclosed in the above patent, it is necessary to find the volume of myocardial tissue and to use a scaling law. In order to use the scaling law, it is essential to perform segmentation of a three-dimensional ventricular model. That is to say, a segmentation work for the entirety of the heart needs to be carried out in order to apply the method of the above patent. Thus, the uncertainty of the model increases. In particular, the ventricular muscle has a complex shape in the thickness direction. This may reduce the accuracy of segmentation.

In the method developed by Kim et al. and the method disclosed in the above patent, an aorta is included in the computational fluid dynamics model (hereinafter referred to as a "CFD model"). The lumped parameter model is composed of a closed circuit including a body artery, a body vein, a pulmonary vein, a left heart, a right heart and the like. For the sake of hemodynamics analysis, the CFD model and the lumped parameter model make use of parameters having some standard representative values. Such parameters (e.g., resistance values and capacitance values for a body artery, a body vein, a pulmonary vein and the like) are not suitable for application to individual patients.

PRIOR ART DOCUMENT

Patent Document

Korean Patent No. 10-1524955 (entitled: patient-specific blood flow modeling method and system)

Non-Patent Document

Pijls, N. H., Van Gelder, B., Van der Voort, P., Peels, K., Bracke, F. A., Bonnier, H. J., Gamal, M. I., 1995. Fractional flow reserve: a useful index to evaluate the influence of an epicardial coronary stenosis on myocardial blood flow. Circulation 92, 3183 e3193.

Kim, H. J., Vignon-Clementel, I. E., Coogan, J. S., Figueroa, C. A., Jansen, K. E., Taylor, C. A., 2010. Patient-specific modeling of blood flow and pressure in human coronary arteries. Ann. Biomed. Eng. 38 (10), 3195 e3209.

Min, J. K., Leipsic, J., Pencina, M. J., Berman, D. S., Koo, B. K., van Mieghem, C., Erglis, A., Lin, F. Y., Dunning, A. M., Apruzzese, P., Budoff, M. J., Cole, J. H., Jaffer, F. A., Leon, M. B., Malpeso, J., Mancini, G. B., Park, S. J., Schwartz, R. S., Shaw, L. J., Mauri, L., 2012. Diagnostic accuracy of fractional flow reserve from anatomic CT angiography. JAMA 308, 1237 e1245.

Koo, B. K., Erglis, A., Doh, J. H., Daniels, D. V., Jegere, S., Kim, H. S., Dunning, A., DeFrance, T., Lansky, A., Leipsic, J., Min, J. K., 2011. Diagnosis of ischemia-causing coronary stenoses by noninvasive fractional flow reserve computed from coronary computed tomographic angiograms. Results from the prospective multicenter DISCOVER-FLOW (diagnosis of ischemia-causing Stenoses obtained via noninvasive fractional flow Reserve) study. J. Am. Coll. Cardiol. 58, 1989 e1997.

Shim, E. B., Chang, K. S., 1997. Numerical analysis of three-dimensional Bj ork-Shiley valvular flow in an aorta. J. Biomech. Eng. 119 (1), 45 e51.

Shim, E. B., Chang, K. S., 1994. Three-dimensional vortex flow past a tilting disc valve using a segregated finite element scheme. Comput. Fluid Dyn. J. 3 (1), 205 e222.

Shim, E. B., Kamm, R. D., Heldt, T., Mark, R. G., 2000. Numerical analysis of blood flow through a stenosed artery using a coupled multiscale simulation method. Comput Cardiol. 27, 219 e222.

Einstein, A., 1906. Eine neue bestimmung der molek dimensionen. Ann. Phys. 19 (2), 289.

Schreiner, W., Neumann, F., Mohl, W., 1990. The role of intramyocardial pressure during coronary sinus interventions: a computer model study. IEEE Trans. Biomed. Eng. 37, 956 e967.

Lim, K. M., Kim, I. S., Choi, S. W., Min, B. G., Won, Y. S., Kim, H. Y., Shim, E. B., 2009. Computational analysis of the effect of the type of LVAD flow on coronary perfusion and ventricular afterload. J. Physiol. Sci. 59 (4), 307 e316.

Brown, A. G., Shi, Y., Marzo, A., Staicu, C., Valverde, I., Beerbaum, P., Lawford, P. V., Hose, D. R., 2012. Accuracy vs. computational time: translating aortic simulations to the clinic. J. Biomech. 45 (3), 516 e623.

Taylor, C. A., Fonte, T. A., Min, J. K., 2013. Computational fluid dynamics applied to cardiac computed tomography for noninvasive quantification of fractional flow reserve: scientific basis. J. Am. Coll. Cardiol. 61 (22), 2233 e2241.

West, G. B., Brown, J. H., Enquist, B. J., 1997. A general model for the origin of allometric scaling laws in biology. Science 276 (5309), 122 e126.

SUMMARY

The present invention provides a novel method and system for blood flow analysis in a blood vessel.

It is a first object of the present invention to provide a novel method and system for analyzing blood flow by applying a CFD model and a lumped parameter model only to a portion of a blood vessel for which blood flow is to be analyzed, instead of using a closed lumped parameter model with respect to the entirety of a body.

It is a second object of the present invention to provide a novel method and system for determining a ratio of flow rates of blood flowing through respective blood vessels branched from an artery, without having to find a volume or a mass of a body region to which blood is supplied by blood vessels branched from an artery.

According to one aspect of the present invention, there is provided a method for determining a fractional flow reserve (FFR) of a coronary artery among cardiovascular information.

A method for determining cardiovascular information using a computer system according to the present invention, includes the steps of: receiving image data including a plurality of coronary arteries originating from an aorta; processing the image data to generate three-dimensional shape models of the coronary arteries; simulating a blood flow for the generated three-dimensional shape models of the coronary arteries; and determining a fractional flow reserve (FFR) of the coronary arteries based on a blood flow simulation result. In the step of simulating the blood flow, a computational fluid dynamics model is applied to the three-dimensional shape models of the coronary arteries, a lumped parameter model is combined with the computational fluid dynamics model, and a simplified coronary artery circulation model including coronary arteries, capillaries of the coronary arteries and coronary veins is used as the lumped parameter model.

In some embodiments, in the step of simulating the blood flow, when applying the computational fluid dynamics model to the three-dimensional shape models of the coronary arteries, an aorta blood pressure pattern may be used as an inlet boundary condition.

In some embodiments, the step of simulating the blood flow may include a step of finding lengths of centerlines of the three-dimensional shape models of the coronary arteries. Resistance values of the capillaries of the coronary arteries may be set based on a ratio of blood flow rates in the coronary arteries when combining the simplified coronary artery circulation model with the computational fluid dynamics model. The ratio of the blood flow rates in the coronary arteries may be set based on a ratio of the lengths of the centerlines of the three-dimensional shape models of the coronary arteries.

According to another aspect of the present invention, there is provided a method for determining a ratio of blood flow rates in blood vessels among blood vessel information.

A method for determining blood vessel information of a patient using a computer system, includes the steps of: receiving image data including at least a part of blood vessels originating from an aorta; processing the received image data to generate three-dimensional models of the blood vessels; finding a length of each of the blood vessels from a branched point to a distal end in a three-dimensional model of each of the blood vessels; and determining a ratio of blood flow rates in the blood vessels depending on a ratio of the lengths of the blood vessels.

The step of finding the length of each of the blood vessels includes: a step of finding a centerline of the three-dimensional model of each of the blood vessels; a step of finding a distal end point where a cross-sectional area of the three-dimensional model of each of the blood vessels is equal to or smaller than a predetermined value; and a step of finding a length of the centerline from the branched of each of the blood vessels a distal end point thereof.

In some embodiments, the blood vessels may include a right coronary artery (RCA), a left anterior descending coronary artery (LAD) and a left circumflex coronary artery (LCX). In the case where the blood vessels are coronary arteries, the ratio of the blood flow rates in the coronary arteries may be determined by the following mathematical formula:

[Mathematical Formula 1]

$$Q_{LAD}:Q_{LCX}:Q_{RCA} = l_{LAD}:l_{LCX}:\cfrac{1}{\cfrac{\alpha}{(l_{RCA})_{RV}} + \cfrac{1}{(l_{RCA})_{LV}}},$$

where $Q_{LAD}$ is a blood flow rate of a left anterior descending coronary artery, $l_{LAD}$ is a length of a left anterior descending coronary artery, $Q_{LCX}$ is a blood flow rate of a left circumflex coronary artery, $l_{LCX}$ is a length of a left circumflex coronary artery, $Q_{RCA}$ is a blood flow rate of a right coronary artery, $l_{RCA}$ is a length of a right coronary artery, $(l_{RCA})_{RV}$ is a length of a portion of a right coronary artery for supplying blood to a right ventricle, $(l_{RCA})_{LEVER}$ is a length of a portion of a right coronary artery for supplying blood to a left ventricle, and $\alpha$ is a correction coefficient of a blood vessel for supplying blood to a right ventricle.

If the ratio of the blood flow rates in the coronary arteries is found based on the ratio of the lengths of the coronary arteries, it is possible to use the ratio of the blood flow rates in order to determine the fractional flow reserve (FFR)

among the cardiovascular information. In the prior art, the resistance values of the capillaries of the coronary arteries for the application of a lumped parameter model are found based on the volumes or masses of the cardiac muscles to which blood is supplied by the coronary arteries. According to the present invention, the resistance values of the capillaries of the coronary arteries for the application of a lumped parameter model can be easily found based on the length of each of the coronary arteries.

In some embodiments, the blood vessels may be arteries for supplying blood to a cerebrum or a cerebellum. For example, the blood vessels may be a cervical artery, a vertebral artery, an external carotid artery, a throat artery, a middle cerebral artery and the like.

According to the present method for determining a fractional flow reserve (FFR) of a coronary artery among cardiovascular information, it is possible to reduce the simulation calculation amount of the computational fluid dynamics model and the lumped parameter model. This makes it possible to shorten the calculation time for the determination of the FFR. This is because the method for determining the cardiovascular information according to the present invention locally simulates the blood flow in the coronary artery using the simplified coronary artery circulation model. In particular, it is possible to reduce the uncertainty of a model for individual patients, which may be generated in the case of using the conventional lumped parameter model which forms a closed circuit with respect to the entirety of a body. In addition, the method for determining a fractional flow reserve (FFR) of a coronary artery according to the present invention presents a simple boundary condition with respect to the shape of a coronary artery. Thus, as compared with the conventional methods, the present method is more efficient in terms of the calculation amount and the calculation time. Moreover, in the method according to the present invention, an aorta is not included in the computational fluid dynamics model. Thus the model according to the present invention is simpler than the model according to the conventional method.

According to the present invention, there is provided a method for determining a ratio of flow rates of blood flowing through a plurality of blood vessels among the blood vessel information. According to the present method, it is possible to determine the ratio of flow rates of blood flowing through the respective branched blood vessels, without having to find the volume or mass of the corresponding body portion to which blood is supplied by the blood vessels branched from the aorta. Accordingly, it is possible to omit the complex calculation for finding a three-dimensional model for the corresponding body portion, which is otherwise required to find the volume or mass of the body portion to which blood is supplied by the respective blood vessels. Since the ratio of flow rates of blood flowing through the blood vessels can be found by performing calculation for finding only the three-dimensional models of the blood vessels, it is possible to reduce the uncertainty which may be generated in the course of finding the three-dimensional model of the body portion.

DETAILED DESCRIPTION

Figure 1:
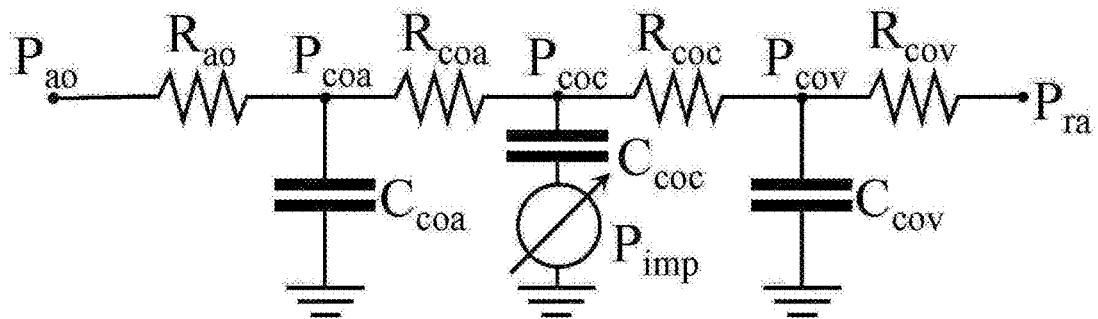
FIG. 1 is a schematic diagram of a simplified coronary circulation model according to the present invention.

Other objects, specific advantages and novel features of the present invention will become more apparent from the following detailed descriptions of preferred embodiments made in conjunction with the accompanying drawings.

Hereinafter, a novel patient-specific model for calculating a fractional flow reserve (FFR) of a coronary artery according to the present invention and a method for determining a fractional flow reserve will be disclosed.

The method according to the present invention uses only the coronary arteries for a computational fluid dynamics model and includes a lumped parameter model of a coronary artery blood vessel system. The method according to the present invention provides a simple boundary condition in respect of the shape of a coronary artery. As compared with the conventional method, the method according to the present invention can reduce the calculation amount and can shorten the calculation time. This method is simpler than the conventional method because an aorta is not included in the model. In order to verify the validity of the method according to the present invention, simulation was performed with respect to a three-dimensional linear blood vessel using a computational fluid dynamics model combined with a lumped parameter model. The result of calculation in the method according to the present invention was compared with the result of simulation performed using only a lumped parameter model. The method according to the present invention was applied to the shape of an actual patient obtained from a clinical trial. A patient-specific model was formed using the CT image data of a patient having stenosis in a coronary artery. The FFR value calculated using the present method was compared with the clinically measured results. In addition, the FFR value was calculated from the CT image data of a patient with respect to a model including an aorta and was compared with the FFR value calculated with respect to a model not including an aorta.

CFD Model for Stenosed Coronary Arteries

An integrated approach was used in which coronary system simulation is connected to a local computational fluid dynamics model of a coronary artery. A model showing a coronary blood vessel extending from a micro coronary artery to a right atrium was used as the lumped parameter model for coronary circulation simulation. A computational fluid dynamics model realized by a finite element method was used in order to simulate a local blood flow in a coronary artery.

In the local computational fluid dynamics model of a stenosed coronary artery, a finite element analysis method using a pressure implicit splitting of operators (PISO) method was utilized in order to calculate a three-dimensional Navier-Stokes equation of a blood flow passing through a stenosed coronary artery. Detailed analysis algorithm is disclosed in a research paper (Shim and Chang, 1994, 1997).

The blood flow was assumed to be an incompressible laminar viscous fluid and was treated as a Newtonian fluid. The density of blood was assumed to be 1,060 kg/m$^3$. The blood viscosity coefficient μ was obtained using the patient's hematocrit value and the Einstein method (Einstein, 1906).

$$\mu = \mu_0(1+2.5 \text{ HCT}) \quad \text{[Mathematical Formula 2]}$$

where HCT denotes the patient's hematocrit value, and to $\mu_0$ denotes the viscosity of plasma substantially equal to the viscosity of water ($\mu_0$=0.0015 kg/ms).

Lumped Parameter Model of Coronary Artery Circulation

The lumped parameter model of coronary circulation was limited to a coronary blood vessel. As shown in FIG. 1, the coronary circulation includes three components, namely a coronary artery (coa), a coronary capillary (coc) and a coronary vein (cov). The lumped parameter model of coronary circulation is composed of elements such as resistors and capacitors and is formulated from the viewpoint of electric analog. The pressure, volume and blood flow of the three components are calculated using hemodynamic parameters related to blood circulation. Unlike other capillary systems, during the systole of a heart, the pressure of a left ventricle around blood vessels becomes very high. Thus, the blood flow rate in a coronary artery decreases. During the diastole, the heart muscles are loosened and the flow of blood toward the capillaries of a left ventricle is not hindered. Thus, the blood flow through a coronary artery becomes free. For the purpose of modeling this mechanism, the internal myocardium pressure of a coronary artery ($P_{imp}$ in FIG. 1) was used. The internal myocardium pressure correlates with the pressure in a ventricle.

$$P_{imp} = \gamma P_{LV} \quad \text{[Mathematical Formula 3]}$$

where $P_{LV}$ is the pressure of a left ventricle and γ is 0.75. The value of γ was presented by Schreiner et al. As will be described below, volume-dependent values were used for resistors $R_{coc}$ and $R_{cov}$ around coronary capillaries.

$$R_{actual} = \begin{cases} R_{original} & \text{if } P_{coc} \leq P_{coa} \\ R_{original} + \beta/V_{coc}^2 & \text{if } P_{coc} > P_{coa} \end{cases} \quad \text{[Mathematical Formula 4]}$$

where $R_{actual}$ is the actual value of $R_{coc}$ or $R_{cov}$, and $R_{original}$ is the basic value of $R_{coc}$ or $R_{cov}$. In the above mathematical formula, β is the empirical constant, and $V_{coc}$ denotes the volume of a coronary capillary. β was set to 0.3 as presented by Schreiner et al.

As represented by mathematical formula 4, the flow of blood in a coronary capillary may be a forward flow (i.e., $P_{coa} > P_{coc}$) or a reverse flow depending on the pressure gradient signal. However, if the volume of a capillary comes close to 0, the blood does not flow out any more. Thus, the backflow is stopped. Moreover, if a capillary is compressed, the resistance is increased and the movement of a blood flow is adjusted. If the volume of a capillary comes close to 0 due to the back pressure gradient, the backflow is reduced to about 0. Detailed contents dealing with a lumped parameter method of coronary circulation are described in an existing study (Schreiner et al., 1990; Shim et al. 2000).

Combination of Computational Fluid Dynamics Model and Lumped Parameter Model

Figure 2:
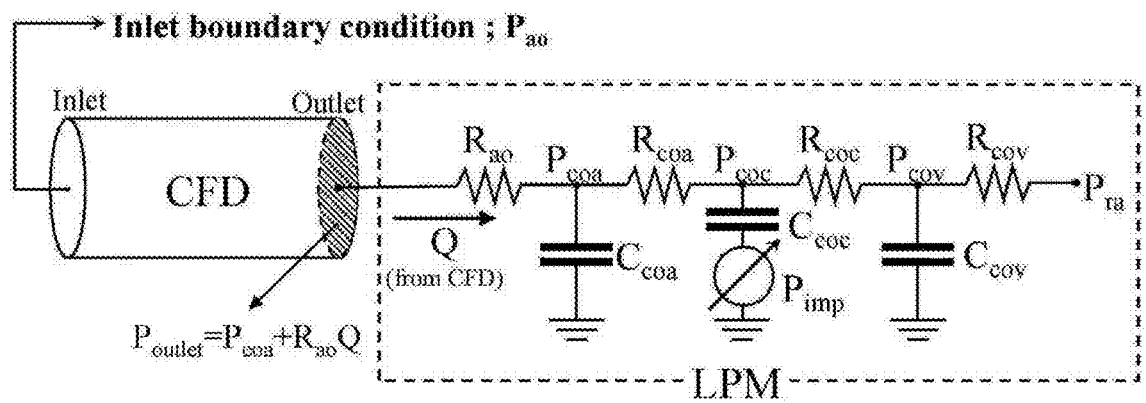
FIG. 2 is a schematic diagram showing a combined relationship between a computational fluid dynamics model and a simplified lumped parameter model.

Furthermore, it was assumed that if a lumped parameter model and a computational fluid dynamics model are combined with each other, the two models affect each other. FIG. 2 schematically shows the combination of the computational fluid dynamics model and the lumped parameter model. The flow rate calculated at the outlet of the computational fluid dynamics model is delivered to the lumped parameter model. The pressures and flow rates of three parts of the lumped parameter model are calculated through an ordinary differential equation (Lim et al., 2009). The blood pressure value of a coronary artery calculated in the lumped parameter model (LPM) is delivered to the computational fluid dynamics model so that the blood pressure value can be used in the next step calculation for calculating $P_{outlet}$ as an outlet boundary condition of the computational fluid dynamics model. Such a combination is effective in analyzing the local fluid dynamics of a large blood vessel connected to micro blood vessels. This is described in detail in a paper (Brown et al., 2012).

Figure 3:
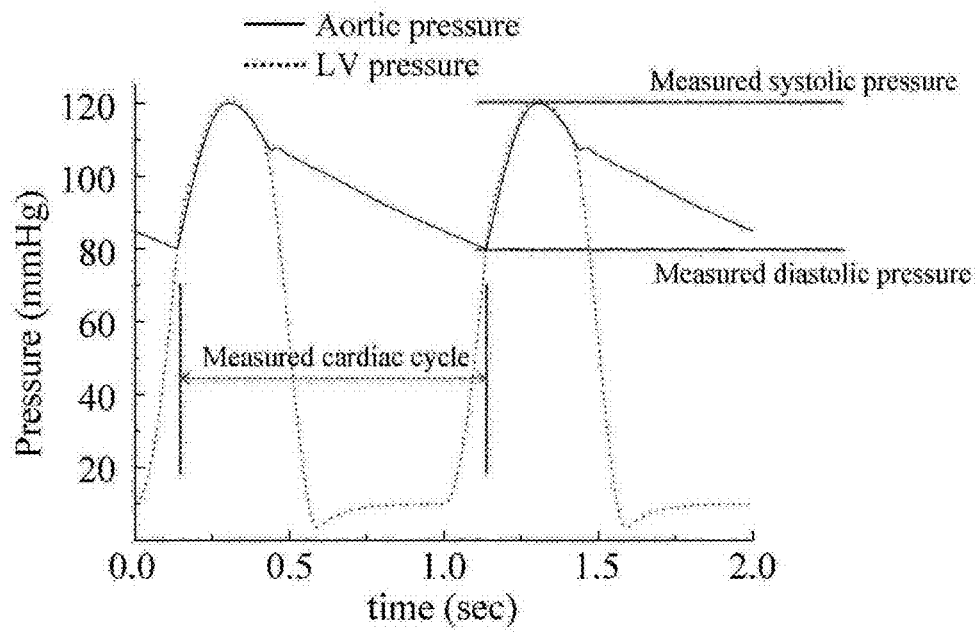
FIG. 3 is a graph showing an example of virtual $P_{ao}$ and $P_{LV}$ in a state in which the heart rate is 65 beats/min and the systolic and diastolic pressures are 120 mmHg and 80 mmHg, respectively, in the present invention.

Unlike the conventional method presented by Kim et al., the method according to the present invention uses an instantaneous pattern of an aorta blood pressure ($P_{ao}$ in FIG. 2) as an inlet boundary condition of the computational fluid dynamics model. Such a pressure pattern was presented in order to match a cardiac cycle with systolic/diastolic blood pressures of a patient. $P_{LV}$ was found by combining a time-dependent capacitance model of a left ventricle with a predetermined temporary pattern of an aorta blood pressure. $P_{LV}$ is used for calculating $P_{imp}$ in mathematical formula 2. FIG. 3 shows an example of virtual $P_{ao}$ and $P_{LV}$ in a state in which the heart rate is 65 beats/min and the systolic and diastolic pressures are 120 mmHg and 80 mmHg, respectively.

Simplified Coronary Artery Three-Dimensional Model

Figure 4:
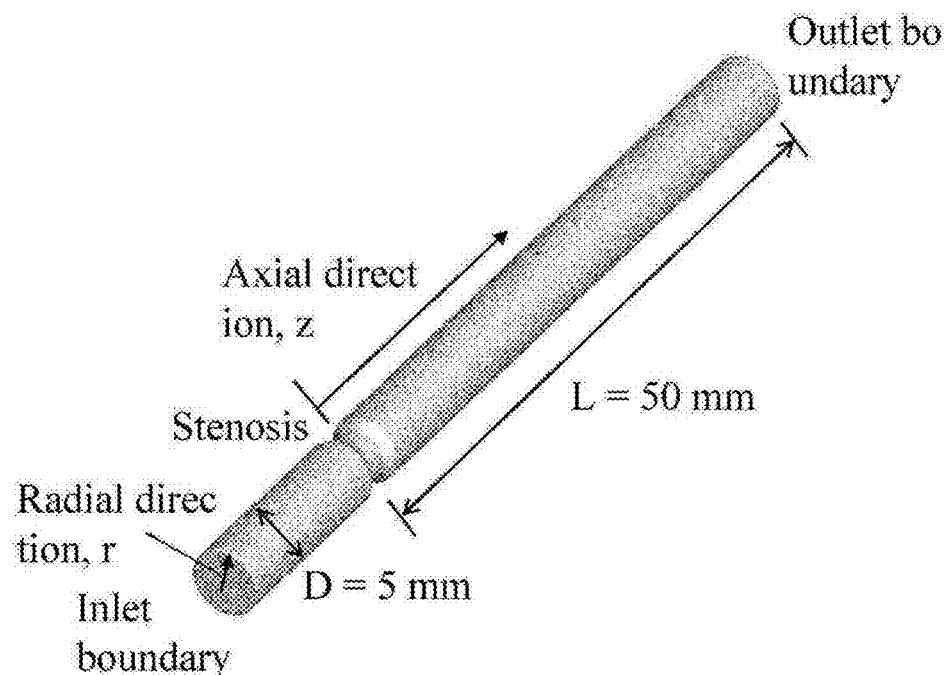
FIG. 4 is a view showing a virtual blood vessel having a diameter ratio ($A_{stenosis}/A_0$) of a stenosed portion of 0.5 and a diameter D of 5 mm in the present invention.

In order to verify the method according to the present invention, as shown in FIG. 4, the result obtained by simulating a slightly stenosed tube (virtual blood vessel) was compared with the result already obtained through a numerical study. The ratio of a stenosed portion to a non-stenosed portion $A_{stenosis}/A_0$ is 0.5 and the diameter D is 5 mm. The density and viscosity of a liquid are 755 kg/m³ and 0.00143 Pa·sec, respectively. The sinusoidal cycle velocity obtained in the existing numerical study was used as an inlet boundary condition.

[Mathematical Formula 5]

$$V_z(r,t) = \frac{\left[3.44 + 2.08\sin\left(\frac{2\pi t}{0.345}\right)\right] \times 10^{-5}}{\pi D^2} \times \left[1 - \left(\frac{2r}{D}\right)^2\right]$$

Figure 5:
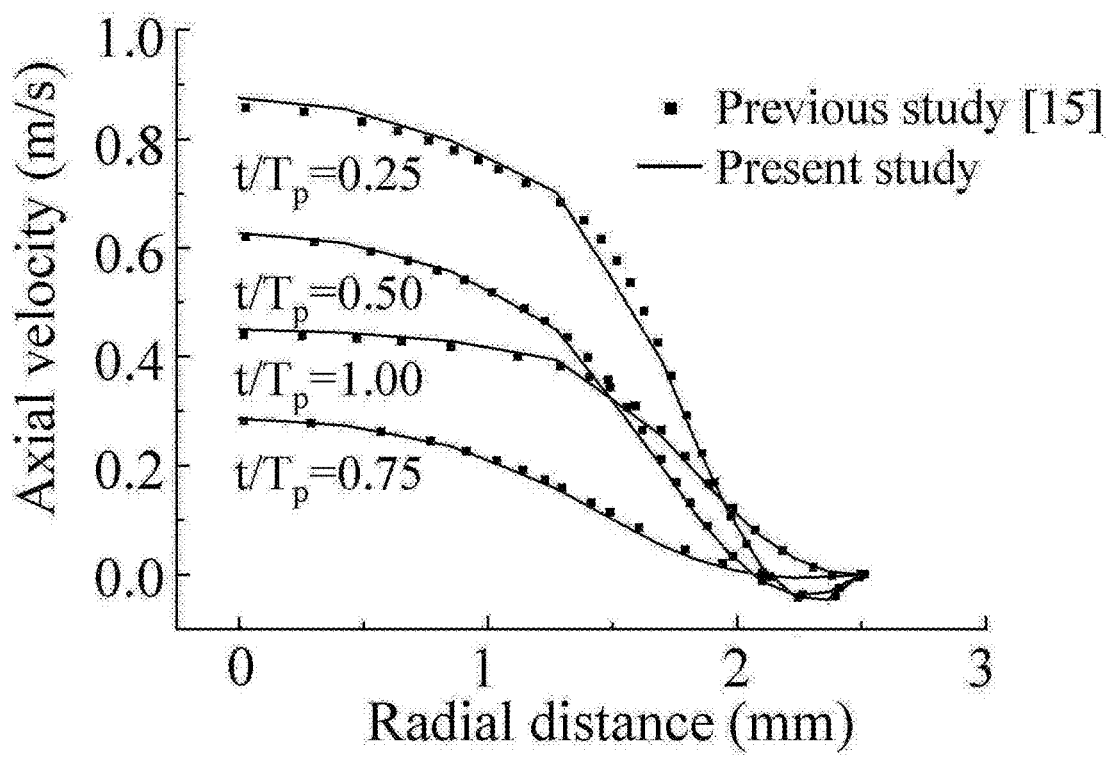
FIG. 5 is a graph showing an axial velocity on a downstream side of a stenosed portion of the virtual blood vessel shown in FIG. 4.

The inlet velocity $V_z$ in mathematical formula 5 is the axial velocity, and D is the diameter of a tube. r and t are the radius and the time, respectively. FIG. 5 shows an axial velocity on a downstream side of a stenosed portion. The sinusoidal cycle velocity was expressed by the formula of $T_p$. The calculated velocity waveform was closely matched with the conventional study result. This shows the temporal and spatial accuracy of the computational fluid dynamics model according to the present invention.

Patient-Specific Model of Coronary Artery

In order to test a simulation model using a clinical actual shape, a patent-specific model was developed by generating three-dimensional shape models of coronary arteries from CT image data. The source of clinical data is Ulsan University Hospital, Republic of Korea. The use of the data obtained from Ulsan University Hospital was approved from IRB. One patient showing stenosis of 50% or more in a major coronary artery having a diameter of 2.5 mm was selected from the patients who have visited the hospital in 2014.

In order to perform segmentation of a CT image, a segmentation program based on activity contour algorithm was developed. The centerline of the coronary artery shape was extracted using the algorithm suggested by Antica et al. The CT image data was refined using the software, Hypermesh™ (http://www.altairhyperworks.com), and a lattice system for three-dimensional analysis was generated. A three-dimensional volume mesh was generated by applying the algorithm of Delaunay to the lattice system thus developed.

Figure 6:
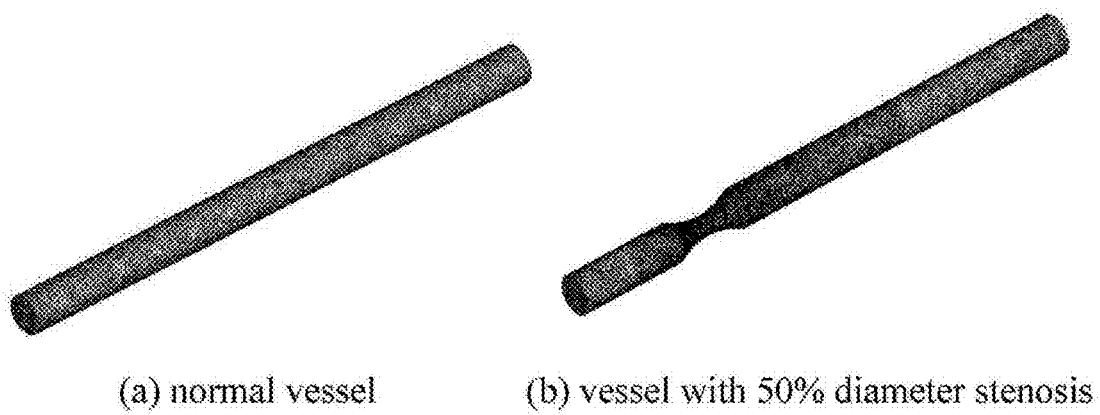
FIGS. 6(a) and 6(b) show three-dimensional geometric models of a virtual blood vessel having no stenosis and a stenosed virtual blood vessel in the present invention.
Figure 7:
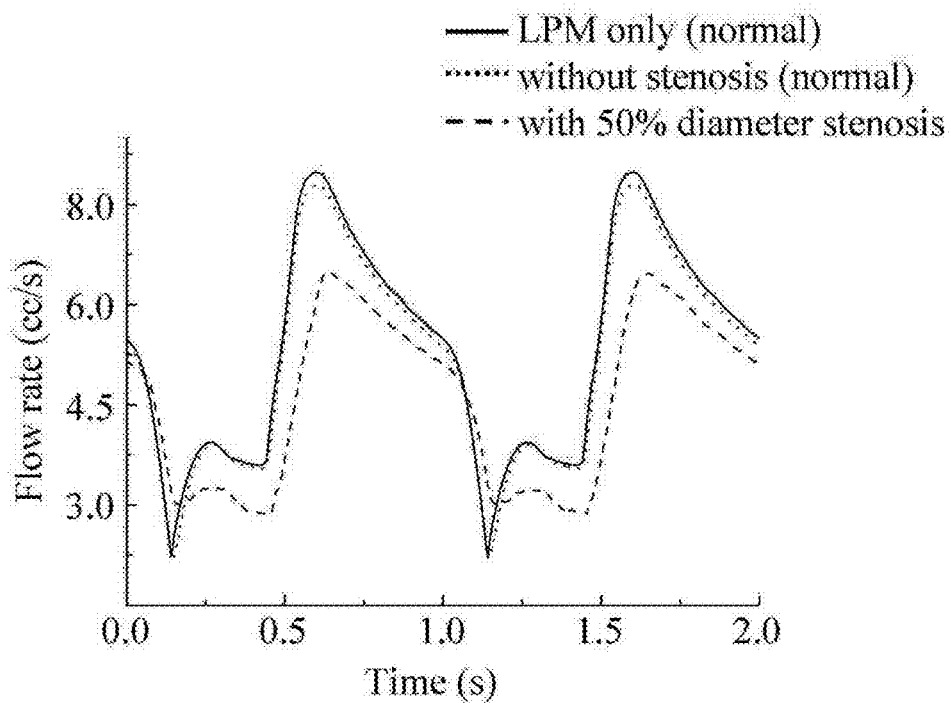
FIG. 7 is a graph showing the flow rates in outlets of coronary arteries of different models.

In order to verify the method for determining cardiovascular information with respect to a simplified three-dimensional model of a coronary artery, the hemodynamic simulation result of a 50%-stenosed liner blood vessel model and a non-stenosed liner blood vessel model imitating a left anterior descending coronary artery was compared with the simulation result of a lumped parameter model. FIGS. 6(a) and 6(b) show 59,353 lattices and 121,292 lattices with respect to non-stenosed blood vessel and a stenosed blood vessel as three-dimensional geometric models. FIG. 7 is a graph in which the outlet flow rates of the two models configured as above and the outlet flow rate of the lumped parameter model are calculated and compared with each other. It was assumed that the average flow rate in a left anterior descending coronary artery (LAD) under a normal state is 1.3 cc/s. The average flow rate in the case of a maximum hyperemia state was increased to 5.2 cc/s, which is four times as high as the flow rate under a normal state. As shown in FIG. 7, the flow rate in the coronary artery is decreased during the ventricular systole and is increased during the ventricular diastole. This result coincides with the waveform of a blood flow velocity in a coronary artery reported in the documents. The model without stenosis and the lumped parameter model are similar in blood flow pattern. However, the 50%-stenosed model has a smaller flow rate than the normal model during the diastole.

Figure 8:
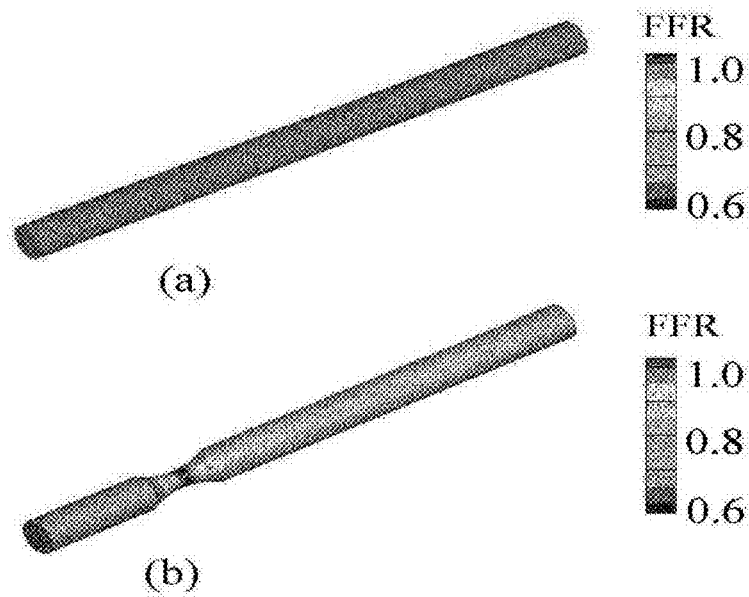
FIGS. 8(a) and 8(b) are contour diagrams showing the FFR values of a virtual blood vessel having 50% stenosis and a virtual blood vessel having no stenosis in the present invention.

FIGS. 8(a) and 8(b) are contour diagrams showing the FFR values of a model having 50% stenosis and a model having no stenosis. The FFR value of the model having no stenosis is about 1.0 in all the portions. In the case of the model having stenosis, it was confirmed that the FFR value (about 0.8) measured on the downstream side of the stenosed portion is reduced. Interestingly, the minimum FFR value of the model having stenosis was observed in the constricted portion of a stenosis lesion.

Figure 9:
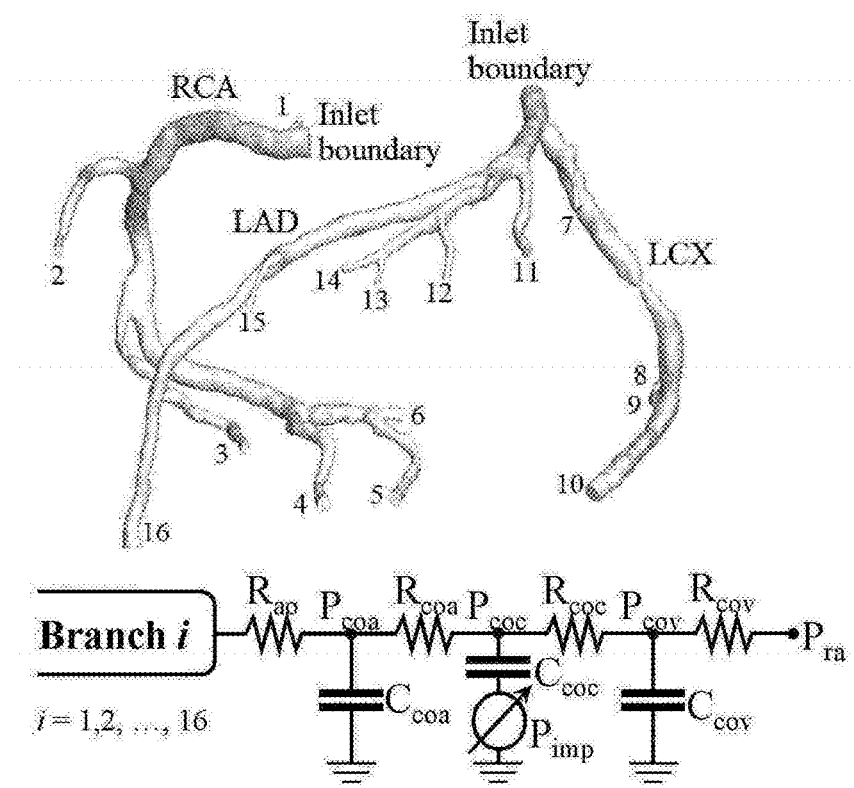
FIG. 9 is a view showing a three-dimensional shape model and a simplified lumped parameter model of coronary arteries of a patient in the present invention.

In order to verify the present method from the viewpoint of a patient-specific model, simulation was conducted for the three-dimensional hemodynamics of a patient who has stenosis in a left circumflex coronary artery (LCX). The three-dimensional structure and boundary condition of this model were described above. FIG. 9 shows a lattice system of a computational fluid dynamics model generated from CT image data of a patient and a lumped parameter model. Table 1 below shows physiological data of a patient required for simulation. For the sake of calculation, a dormant cardiac output measured by a stroke volume and a heart rate was found at first. It was assumed that the total flow rate of a coronary artery is 4% of the cardiac output. In order to establish a maximum hyperemia state, the flow rate of a coronary artery was increased to four times of the flow rate in a dormant state. The resistance value of each coronary artery vessel was calculated based on the total flow velocity of a coronary artery and the cross-sectional area of each branch. Similarly, the capacitance value was determined according to the conventional method. Table 2 shows the total resistance values and the capacitance values of a left anterior descending coronary artery (LAD), a left circumflex coronary artery (LCX) and a right coronary artery (RCA) in the lumped parameter model. The specified pattern of an aorta pressure defined by the heart rate of a patient measured from the systolic/diastolic blood pressures in the inlet of a coronary artery is shown in FIG. 3.

TABLE 1

| Diastolic BP (mmHg) | Systolic BP (mmHg) | HR | Hematocrit (%) | Stroke volume (ml) |
|---|---|---|---|---|
| 66 | 133 | 58 | 34.1 | 59.9 |

TABLE 2

| | $R_{ao}$ | $R_{coa}$ | $R_{coc}$ | $R_{cov}$ | Unit. R = mmHg * s/ml, C = ml/mmHg | | |
|---|---|---|---|---|---|---|---|
| | | | | | $C_{coa}$ | $C_{coc}$ | $C_{cov}$ |
| RCA | 8.0276 | 13.044 | 2.6759 | 1.3379 | 5.89E−04 | 3.73E−03 | 7.47E−03 |
| LCX | 2.2038 | 3.5812 | 0.7346 | 0.3673 | 1.88E−03 | 1.19E−02 | 2.38E−02 |
| LAD | 2.3013 | 3.7397 | 0.7671 | 0.3835 | 1.53E−03 | 9.70E−03 | 1.94E−02 |

Figure 10:
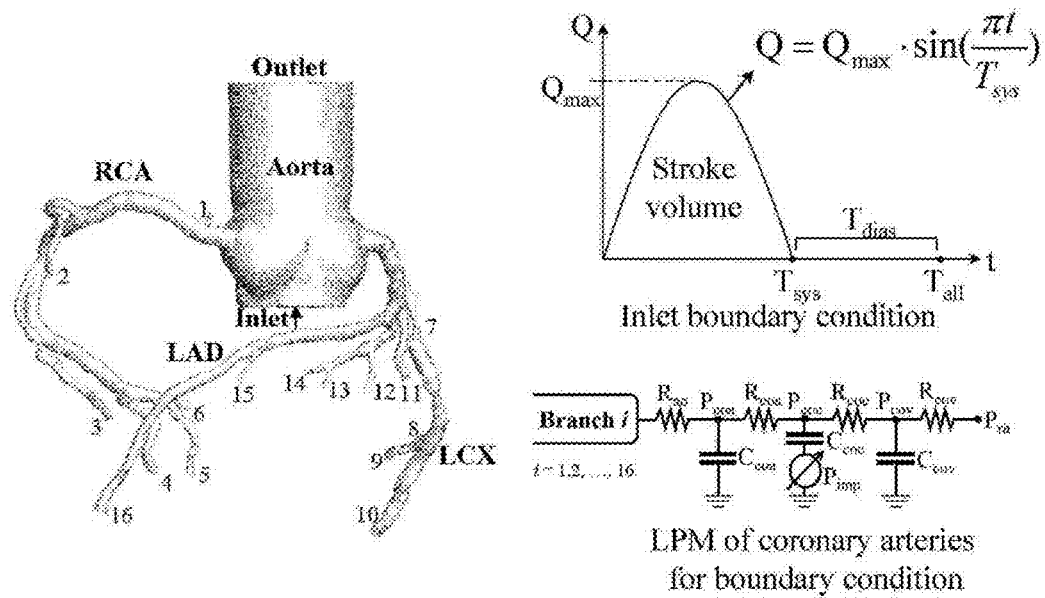
FIG. 10 is a view showing a coronary artery model including an aorta, a lumped parameter model and a flow pattern in an aorta in the present invention.

In order to evaluate the influence of the simulated FFR value on the aorta portion, simulation was conducted with respect to the model including an aorta. In the model including an aorta, inlet and outlet boundary conditions of an aorta need to be designated although an inlet boundary condition of a coronary artery is designated in a model having no aorta. It was assumed that the flow pattern from a left ventricle to an aorta is a sinusoidal curve having a maximum flow rate $Q_{max}$ as shown in FIG. 10. Qmax can be calculated based on the measured cardiac output and cardiac cycle. The velocity pattern on an inlet plane was defined using an inlet flow rate as shown in FIG. 10. It is assumed that the spatial velocity distribution on the inlet plane is uniform. In the study conducted by Kim et al., the outlet of an aorta is connected to a component of a lumped parameter model of the whole cardiovascular system. In the method according to the present invention, a specific pattern of an aorta pressure was used as the outlet boundary condition.

Figure 11:
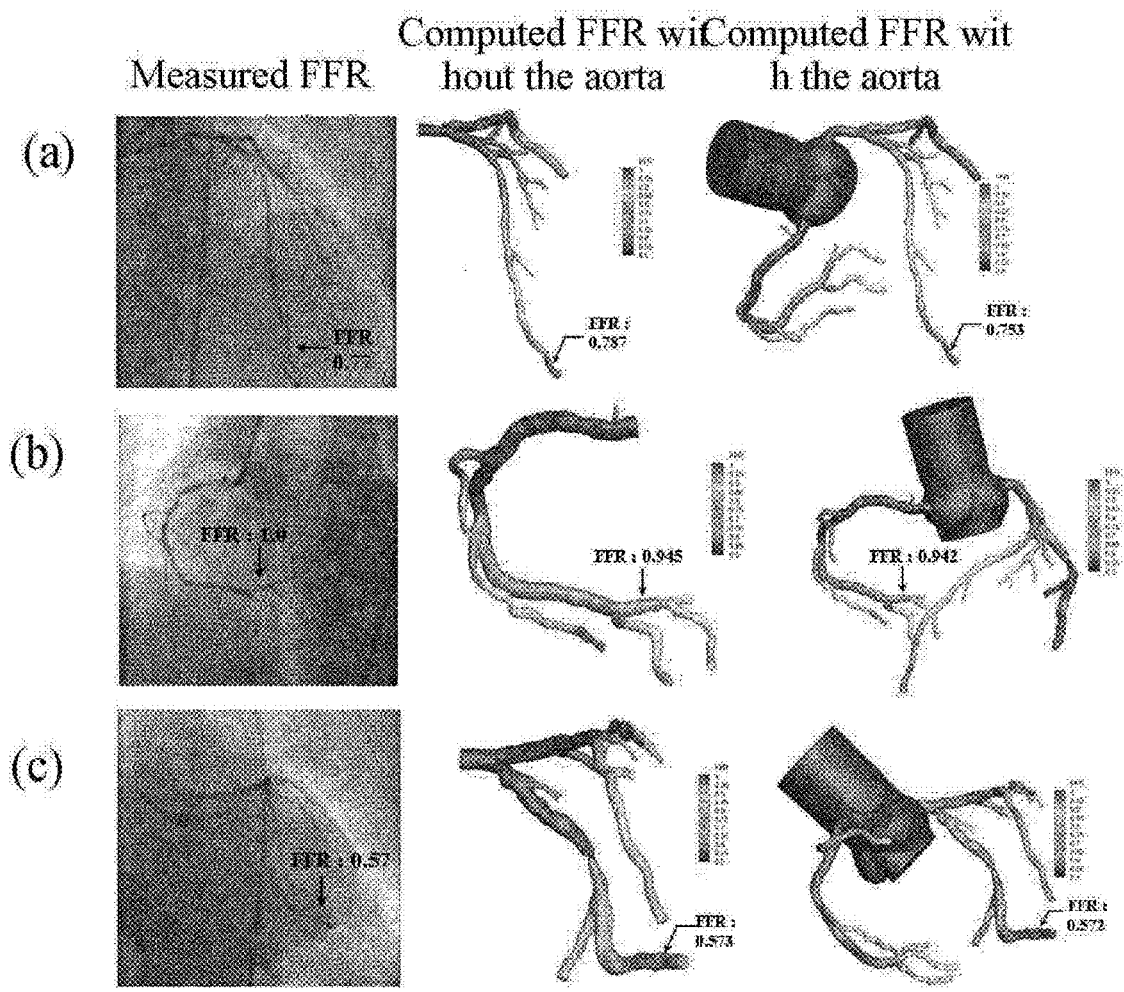
FIGS. 11(a), 11(b) and 11(c) are views in which the FFR values calculated for a model excluding an aorta and a model including an aorta are compared with clinical data in the present invention.
Figure 12:
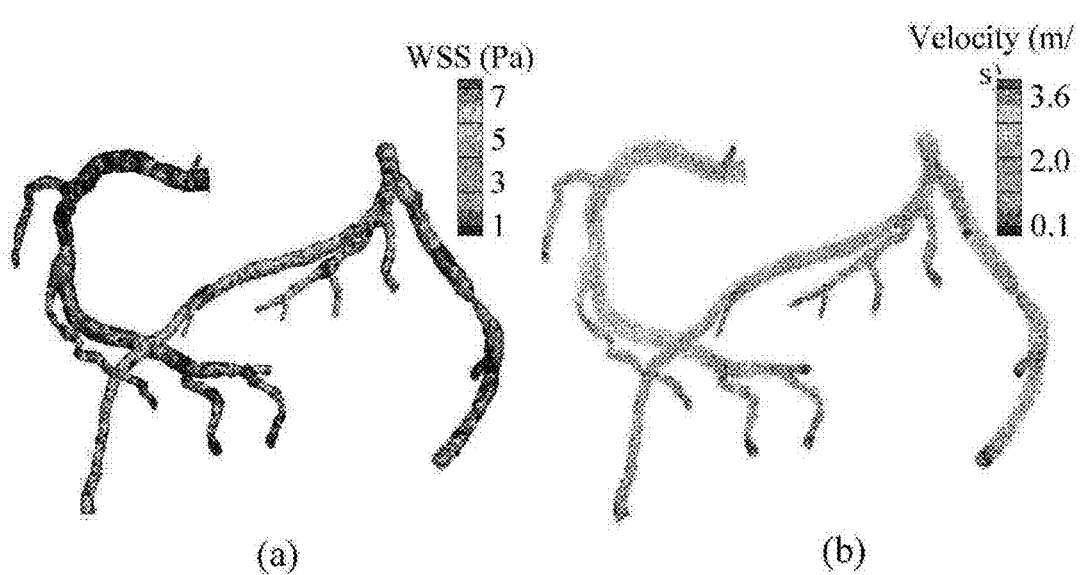
FIGS. 12(a) and 12(b) are views showing WSS distributions at the maximum flow rate in a left anterior descending artery in the present invention.

Table 3 indicated below shows the calculated time according to the number of mesh points and the cardiac cycle. The calculation is more efficient in the model without the aorta than in the model with the aorta. FIG. 11 shows the calculated FFR values of the two models and the measured clinical data values. The clinical FFR was measured by a pressure guide-wire (Pressure Wire Certus, St. Jude Medical Systems, Uppsala, Sweden). The FFR values measured in the left anterior descending coronary artery (LAD), the left circumflex coronary artery (LCX) and the right coronary artery (RCA) are substantially similar in three cases. In addition, the FFR contour pattern of the model not including the aorta is substantially the same as the FFR contour pattern of the model including the aorta. The wall shear stress and the velocity vector calculated at the maximum flow rate in the left anterior descending coronary artery (LAD) are shown in FIG. 12. The shear stress is highest near the stenosed portion of the left circumflex coronary artery (LCX).

TABLE 3

| | The model without the aorta | The model with the aorta |
|---|---|---|
| The number of the mesh points in the CFD model | 132,120 | 193,672 |
| Consumed computational time (min) for a cardiac cycle | 93.2 | 164.7 |

Used computer: PC Intel i7-3770K CPU 3.5 GHz
No parallel processing for the CFD code The FFR simulation is non-invasive and safe and, therefore, is very useful for evaluating the functional degree of the coronary artery stenosis. The existing methods for FFR simulation include the lumped parameter method of the aorta and the whole cardiovascular system in the computational fluid dynamics model, consequently requiring a large calculation amount and a large calculation time. However, for the purpose of efficient application to the clinic, the FFR simulation method should be so simple and rapid that it can be executed in a personal computer. The present invention provides a novel and effective method for calculating an FFR value of a stenosed coronary artery.

The method according to the present invention has some apparent differences from the conventional methods. First, the computational fluid dynamics model applied to the present method does not include an aorta. Thus, the present method does not require the boundary conditions of an inlet and an outlet of an aorta respectively connected to a left ventricle and a body circulation system. Secondly, the lumped parameter model applied to the present method is not a closed circuit. In the lumped parameter system, the closed circuit model has to include, as lumped parameters, a body artery, a body vein, a pulmonary vessel, a vein, a left heart and a right heart. Furthermore, there is a lumped parameter component for a coronary artery circulation system. However, the configuration of the lumped parameter model applied to the present invention includes only a coronary artery micro vessel system (a coronary artery, a coronary capillary and a coronary vein). The conventional computational fluid dynamics model using an aorta and a closed circuit of a lumped parameter method requires some parameters (resistance values and capacitance values of a body artery, a body vein, a pulmonary vessel, a vein, a left heart and a right heart). Such individual parameters have representative values in a reference case. However, in the case of applying the parameters to a patient-specific case, it is hard to say that the parameters are patient-specific. The present method does not include an aorta. A specified pressure pattern is applied to the inlet condition of computational fluid dynamics of a coronary artery. The specified pressure pattern is extracted from the clinically measured blood pressure as shown in FIG. 3. Thus, the respective parameters of a lumped parameter model for a closed circuit model are not required in the model to which the present method is applied. Accordingly, the uncertainty of the model is reduced.

From the viewpoint of calculation, the present method has some advantages. As shown in Table 3, the number of three-dimensional mesh points of the model not including the aorta is smaller than that of the model including the aorta. This contributes to the calculation efficiency of the present model. Furthermore, the conventional methods are based on the combination of the computational fluid dynamics model of the aorta with the whole circulation lumped parameter model. This requires a repetitive interaction between the two models at each time stage. In the present method, the computational fluid dynamics model of the aorta and the lumped parameter model of the whole cardiac vessel are replaced by the specified boundary condition of the computational fluid dynamics model of the coronary artery. This does not require the repetitive calculation between the computational fluid dynamics model of the aorta and the lumped parameter model. From the viewpoint of calculation accuracy, the present method shows a very reasonable result as compared with the conventional method. In a linear blood vessel, the outlet flow rate of the computational fluid dynamics model is substantially the same as the value calculated in the lumped parameter model. In contrast, the flow rate and the FFR in the case of existence of stenosis are smaller than those of a normal case. As shown in FIG. 7, the average flow rate calculated through the 50% stenosis is similar to the experimental measurement result. This indicates the calculation accuracy of the present method.

In the three-dimensional patient-specific model, the shape of the coronary artery was extracted from the patient CT data. Furthermore, the resistances and capacitances of the entire coronary arteries are obtained and are redistributed to the branches of the coronary arteries depending on the ratio of the total coronary artery flow rate to the cross-sectional areas of the branches of the coronary artery. As shown in FIGS. 11(a), 11(b) and 11(c), the calculated results of the FFR values in the right coronary artery, the left circumflex coronary artery and the left anterior descending coronary artery coincide with the clinically measured results. Interestingly, the calculation result of the model having the aorta is substantially the same as the calculation result of the model having no aorta. This means that the aorta does not affect the calculated FFR value of the coronary artery. The high wall shear stress in the coronary artery means the high possibility of plaque growth or plaque breakage. Thus, the distribution of the wall shear stress is an important variable in the stenosed coronary artery. FIGS. 12(a) and 12(b) show the WSS distribution at the maximum flow rate in the left anterior descending artery. This means that the diagnosis lesion has a relatively high value.

Method for Determining a Ratio of Flow Rates of Blood Flowing Through a Plurality of Blood Vessels Branched from an Artery In order to analyze the blood flow in the coronary artery or the cerebral vessel, it is necessary to find the distribution ratio of the blood flow rates with respect to the blood vessels branched from the artery. The ratio of the flow rates of the blood flowing through the branches of the coronary artery becomes a base for setting the resistance value of the lumped parameter model connected to each of the coronary artery branches at the time of calculating the CT-FFR. The distribution of blood flow rates to a plurality of branched blood vessels varies depending on the patient. Thus, a patient-specific method is required for the distribution of blood flow rates.

According to another aspect of the present invention, there is provided a method for setting the ratio of blood flow rates in the coronary artery branches depending on the patient. This helps enhance the accuracy and convenience of a simulation technique for CT-FFR analysis or the like.

The total flow rate of the blood flowing toward the coronary arteries is largely divided into three flow rates LAD, LCX and RCA. The flow rate $Q_{total}$ of the blood flowing through the entire coronary arteries is distributed to the respective branches at the ratio which varies depending on the patient. If the ratio of the flow rates of the blood flowing through the coronary arteries of the patient can be found, it is possible to set the resistance by the cardiac peripheral vessels of the patient. The flow rate of the blood flowing through the coronary arteries of the patient may be represented by the following mathematical formula 6.

$$Q_{total} = Q_{LAD} + Q_{LCX} + Q_{RCA} \qquad \text{[Mathematical Formula 6]}$$

Using mathematical formula 6, the relationship between the flow rate of the blood flowing through the coronary arteries, the blood pressure and the resistance may be represented by the following mathematical formula 7.

$$Q_{LAD} = \frac{\Delta P}{R_{LAD}} \qquad \text{[Mathematical Formula 7]}$$

$$Q_{LCX} = \frac{\Delta P}{R_{LCX}}$$

$$Q_{RCA} = \frac{\Delta P}{R_{RCA}}$$

Figure 13:
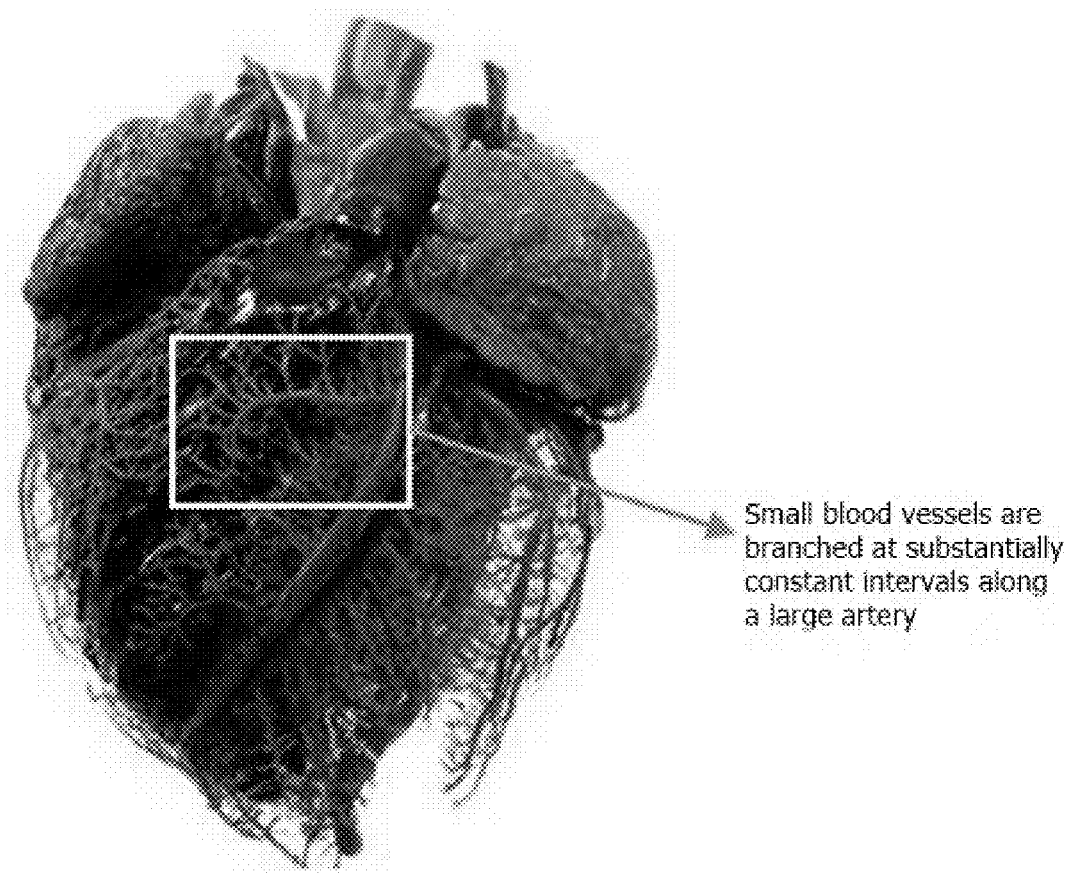
FIG. 13 is a view showing a blood vessel distribution in a heart.

In mathematical formula 7, $\Delta P$ refers to the difference between the pressure at the location where the coronary arteries are branched from the aorta and the pressure at the ventricle to which the blood flowing through the cardiac muscles are finally returned. As shown in FIG. 13, the coronary arteries are distributed in the heart in such a way that the arteries having a small diameter are branched from the arteries having a large diameter. The cardiovascular photograph shown in FIG. 13 is cited from http://www.plastinate.com/leistungen/ausgussp1.htm. The blood flow resistance of the blood vessels distributed as shown in FIG. 13 will now be described. According to the assumption of Poiseuille, the resistance of a blood vessel is inversely proportional to the fourth power of the diameter. Thus, the resistance is quite larger in the blood vessels having a smaller diameter than in the blood vessels having a larger diameter. Accordingly, the resistance in the coronary arteries having a large diameter is negligible. Therefore, even if the modeling is performed in consideration of only the resistance of the blood vessels having a small diameter, there is no great difference between the resistance obtained by the modeling and the actual resistance.

Figure 14:
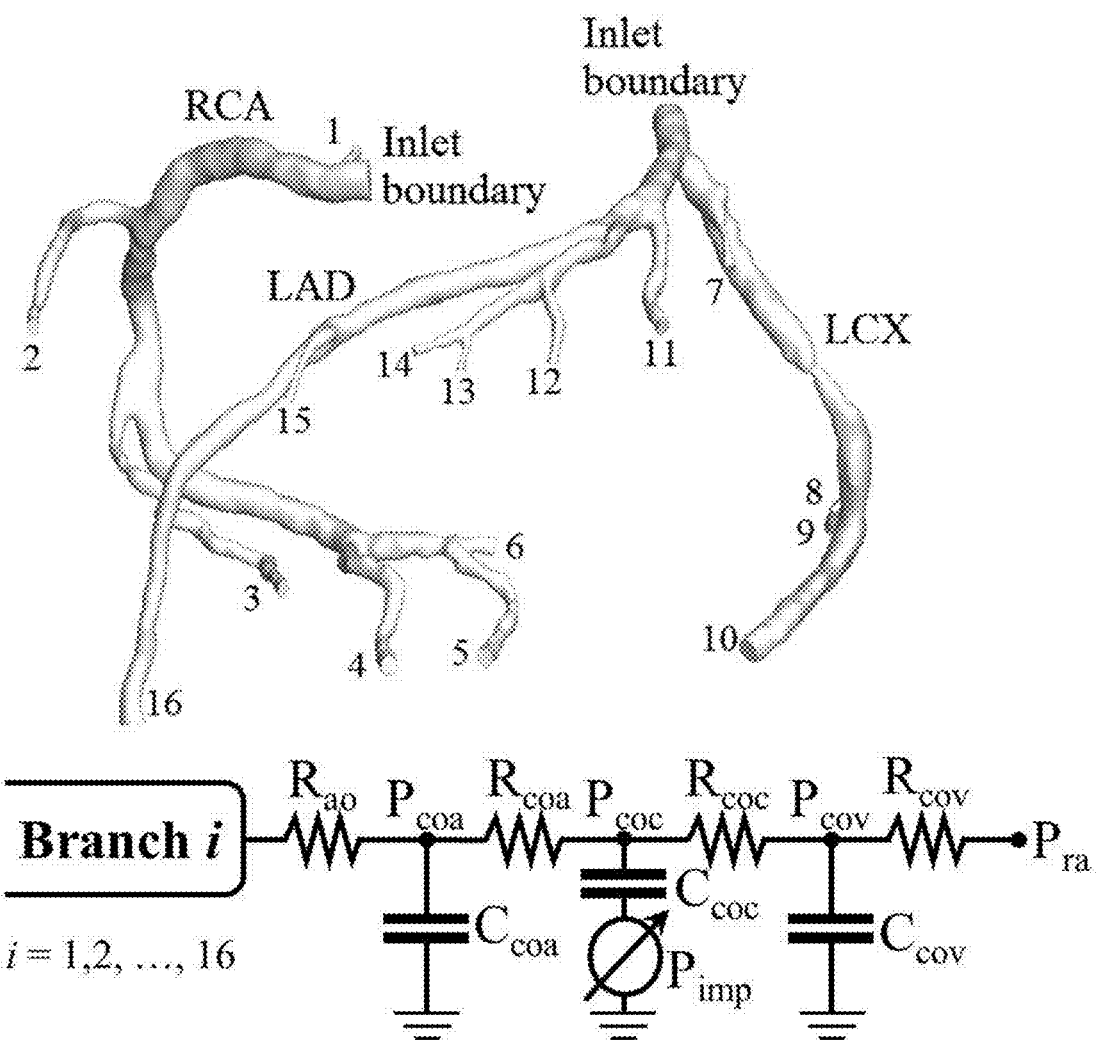
FIG. 14 is a schematic diagram of micro blood vessels branched from a main blood vessel of a coronary artery.
Figure 15:
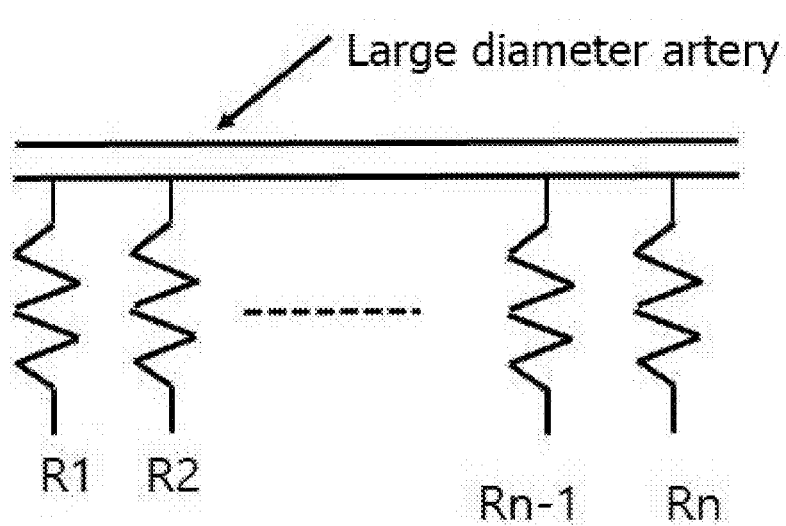
FIG. 15 is a schematic diagram showing the resistors of micro blood vessels branched from a blood vessel having a large diameter.

FIG. 14 schematically shows the blood vessel distribution of the coronary arteries shown in FIG. 13. Referring to FIG. 14, it is assumed that n branched blood vessels having a small diameter are parallel-connected to the coronary arteries having a large diameter. In this case, if only the resistances of the blood vessels having a small diameter are taken into account, the total resistance of the coronary arteries and the branched vessels may be represented by the following mathematical formula 8.

$$\frac{1}{R} = \frac{1}{R_1} + \frac{1}{R_2} + \frac{1}{R_3} + \frac{1}{R_4} + \ldots + \frac{1}{R_n} \qquad \text{[Mathematical Formula 8]}$$

If it is assumed that the resistances of the blood vessels having a small diameter are equal to each other in mathematical formula 8, resistance R can be found by the following mathematical formula 9.

$$R = \frac{R_1}{n} \qquad \text{[Mathematical Formula 9]}$$

Referring to FIG. 13, the blood vessels having a small diameter are branched from the coronary artery at substantially constant intervals. Thus, the number n of the branched blood vessels having a small diameter is proportional to the length of the length of the coronary artery having a large diameter. Accordingly, the resistance of the coronary arteries may be represented by the following mathematical formula 10.

$$R = k\frac{R_1}{l} \qquad \text{[Mathematical Formula 10]}$$

In the above formula, k is the arbitrary proportional constant and the l is the length of the coronary artery. It can be assumed that the proportional constant k and the resistance $R_1$ of the blood vessel having a small diameter are substantially equal in the case of the LAD and the LCX which supply blood to the cardiac muscles of the left ventricle. In reality, it is known that the anatomical patterns of micro blood vessels of the coronary artery in the left ventricle are substantially identical in all locations.

If mathematical formula 10 is applied to the coronary artery for supplying blood to the left ventricle shown in FIG. 7, the following mathematical formula 11 is obtained.

$$Q_{LAD} = \frac{l_{LAD} \Delta P_{LAD}}{kR_1} \qquad \text{[Mathematical Formula 11]}$$

$$Q_{LCX} = \frac{l_{LCX} \Delta P_{LCX}}{kR_1}$$

However, the situation is somewhat complex in the case of the RCA. In the case of the RCA, a blood vessel for supplying blood to the right ventricle and a blood vessel for supplying blood to the left ventricle coexist. Thus, if it is assumed that the blood vessel for supplying blood to the right ventricle and the blood vessel for supplying blood to the left ventricle are connected to each other in the case of the RCA, the resistance of the RCA may be represented by the following mathematical formula 12.

$$R_{RCA} = \left(\frac{R_1}{n}\right)_{RV} + \left(\frac{R_1}{n}\right)_{LV} \qquad \text{[Mathematical Formula 12]}$$

In mathematical formula 12, in the case of the blood vessel for supplying the left ventricle (indicated by LV in the formula), the same values as those of the LAD and the LCX may be used as the n value and the value of the proportional constant k. On the other hand, the same n value and the same value of the proportional constant k cannot be used with respect to the blood vessel for supplying the blood to the right ventricle. While the left ventricle generates a high pressure in order to pump blood toward the whole body, the right ventricle generates a relatively low pressure because it is only necessary for the right ventricle to supply blood to the lung. In reality, the blood flow pressure in the left ventricle is as high as about 100 mmHg. However, the blood flow pressure in the right ventricle is ⅓ to ¼ of the blood flow pressure in the left ventricle. Thus, the muscular layer of the right ventricle is thinner than the muscular layer of the left ventricle. In addition, the density of the branched blood vessels is lower in the right ventricle than in the left ventricle. Thus, the number of the blood vessels having a small diameter, which are branched per unit length of the artery, is small in the portion of the RCA which supplies blood to the right ventricle. Accordingly, as for the blood vessels for supplying blood to the right ventricle, the resistance in the RCA can be found as in the following mathematical formula 13 by dividing the n value by a constant α larger than 1.

$$R_{RCA} = \left(\frac{R_1}{n/\alpha}\right)_{RV} + \left(\frac{R_1}{n}\right)_{LV} = \qquad \text{[Mathematical Formula 13]}$$

$$k\alpha \frac{R_1}{(l_{RCA})_{RV}} + k\frac{R_1}{(l_{RCA})_{RV}}$$

By substituting mathematical formula 13 into mathematical formula 7 on the RCA, it is possible to find the flow rate of the blood flowing through the RCA as represented by the following mathematical formula 14.

$$Q_{RCA} = \frac{\Delta P_{RCA}}{R_{RCA}} = \frac{1}{kR_1}\frac{\Delta P_{RCA}}{\frac{\alpha}{(l_{RCA})_{RV}} + \frac{1}{(l_{RCA})_{LV}}} \qquad \text{[Mathematical Formula 14]}$$

In mathematical formulae 10 and 14, $\Delta P$ refers to the difference between the aorta pressure and the pressure at the ventricle to which the blood flowing through the cardiac muscles are finally returned. Thus, $\Delta P$ remains the same for the coronary arteries LAD, LCX and RCA. Accordingly, the ratio of the flow rates in the respective coronary arteries may be represented by the following mathematical formula 15.

$$Q_{LAD}:Q_{LCX}:Q_{RCA} = \qquad \text{[Mathematical Formula 15]}$$

$$l_{LAD}:l_{LCX}:\frac{1}{\frac{\alpha}{(l_{RCA})_{RV}} + \frac{1}{(l_{RCA})_{LV}}}$$

By finding the lengths of the blood vessels LAD, LCX and RCA, it is possible to know the ratio of the flow rates in the respective branches from mathematical formula 15. Then, by distributing the flow rates in the coronary arteries (about 4% of the total cardiac output) according to the ratio of the flow rates in the respective branches, it is possible to estimate the flow rates of the blood flowing through the respective coronary arteries. In addition, the value of the total vessel resistance (the resistance in the lumped parameter model) for the respective coronary arteries can be set based on the estimated flow rates in the respective coronary arteries.

Method for Finding the Length of a Blood Vessel from a Three-Dimensional Shape Model of a Coronary Artery Descriptions will now be made on a method for finding the length of a blood vessel from a three-dimensional shape model of a coronary artery and determining the ratio of flow rates in the respective blood vessels according to one embodiment of the present disclosure. According to the present method, the ratio of the flow rates in the respective coronary artery branches can be estimated by finding the length of the respective coronary artery branches instead of finding the volume of the cardiac muscles to which blood is supplied by the coronary arteries LAD, LCX and RCA. Accordingly, when determining the patient-specific cardiovascular information such as the FFR or the like, it is not necessary to perform an image analysis procedure of CT image data for finding the volume of cardiac muscles of the left ventricle.

In the case of applying the present method, the blood flow rate is calculated by calculating only the length of each coronary artery using the three-dimensional model of the coronary artery extracted from the CT image data to realize the computational fluid dynamics model. Accordingly, it is possible to reduce the calculation amount required for analyzing the three-dimensional model of the coronary artery, thereby shortening the calculation time.

Figure 16:
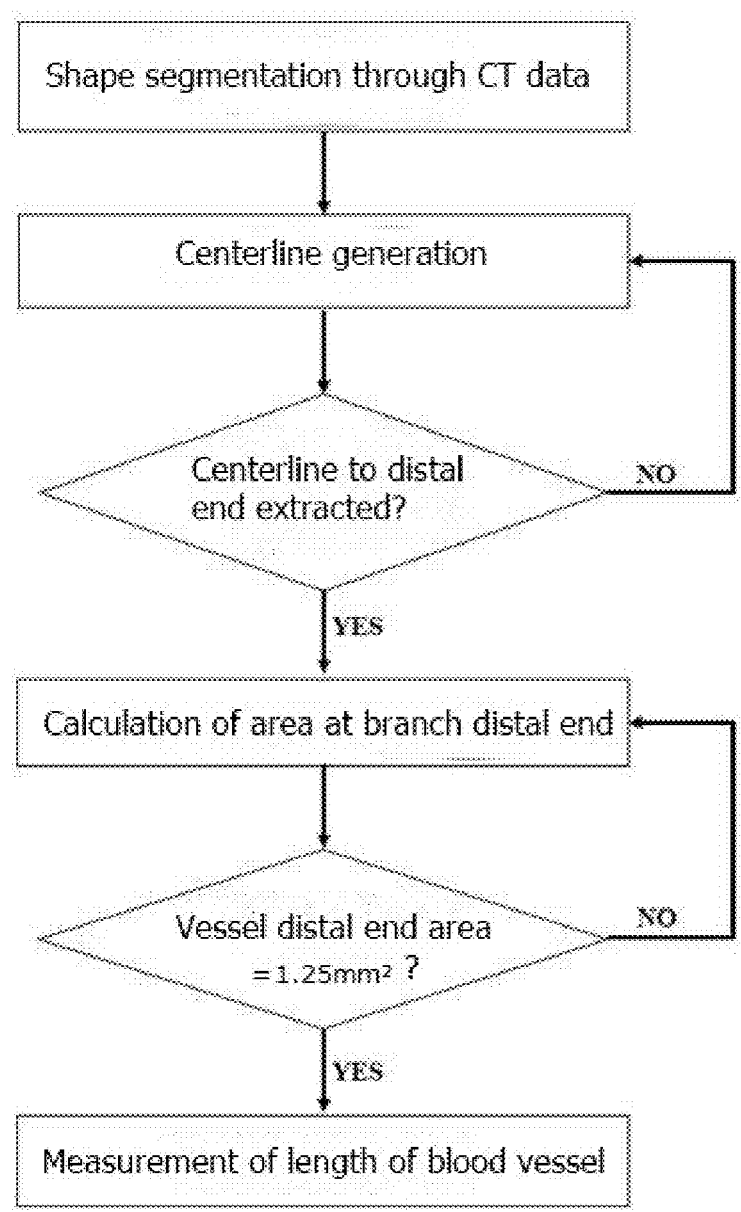
FIG. 16 is a flowchart explaining a method of finding a length of a blood vessel according to the present invention.

Referring to FIG. 16, the length of the coronary artery is found from the three-dimensional model of the coronary artery in the following order.

1) A three-dimensional shape model of a coronary artery is generated by processing CT image data.

2) A centerline of a coronary artery is generated from the three-dimensional shape model of the coronary artery.

3) An area of a distal end of the generated centerline is calculated and a point where the calculated area is equal to or smaller than a predetermined area is selected as a distal end point.

4) The length of the centerline from the branched point of the coronary artery to the distal end point thereof.

In the case where the coronary artery is an RCA, the length of the coronary artery is found in the following order.

5) The length of the RCA is measured, at which time the length to a branched point of a PLA (posterior lateral artery) and a PDA (posterior descending artery) and the length from the branched point to the distal end are calculated.

6) The length to the branched point of the PLA and the PDA is divided by a predetermined value (between ⅓ and ¼) to correct the length.

7) Since the PLA and the PDA supply blood to the left ventricle, the length of the PLA and the PDA is calculated in the same manner as the length of the LAD and the LCX.

Calculation of the Blood Flow Rates in the Coronary Arteries Using the Length of the Coronary Arteries In order to verify the validity of the present method, the estimation result of the blood flow rate in the coronary artery estimated using the volume of the cardiac muscles was compared with the calculation result of the blood flow rate in the coronary artery calculated according to the present method.

The CT image data provided by Ulsan University Hospital, Republic of Korea, was used for the verification. Aquarius of Terarecon, Inc., which is commercially available image processing software, was used to calculate the volume of the cardiac muscles to which blood is supplied by the respective coronary artery branches. The length of each coronary artery was calculated with respect to the CT image data (50 blood vessels for 25 patients) provided by Ulsan University Hospital. The blood flow rate in each coronary artery was estimated based on the calculated length of each coronary artery. Table 4 shows the blood flow rates in the respective coronary arteries estimated on the basis of the blood vessel length. In Table 4, the blood flow rates in the coronary arteries estimated on the basis of the volumes of the cardiac muscles are denoted by $Flow_{volume}$. The blood flow rates in the coronary arteries estimated on the basis of the length of the blood vessels are denoted by $Flow_{length}$.

TABLE 4

| case | $Flow_{length}$ (%) | | | $Flow_{volume}$ (%) | | |
| --- | --- | --- | --- | --- | --- | --- |
| | RCA | LCX | LAD | RCA | LCX | LAD |
| 1 | 27 | 41 | 33 | 29 | 33 | 38 |
| 2 | 34 | 32 | 34 | 34 | 28 | 38 |
| 3 | 34 | 27 | 40 | 30 | 30 | 40 |
| 4 | 43 | 25 | 32 | 33 | 28 | 39 |
| 5 | 31 | 27 | 42 | 33 | 23 | 45 |
| 6 | 21 | 36 | 44 | 28 | 28 | 45 |
| 7 | 33 | 25 | 43 | 33 | 26 | 41 |
| 8 | 34 | 35 | 31 | 28 | 33 | 38 |
| 9 | 28 | 38 | 34 | 30 | 35 | 36 |
| 10 | 26 | 37 | 38 | 28 | 34 | 38 |
| 11 | 35 | 14 | 51 | 32 | 15 | 53 |
| 12 | 30 | 37 | 33 | 28 | 37 | 35 |
| 13 | 31 | 24 | 45 | 29 | 30 | 41 |
| 14 | 25 | 43 | 32 | 29 | 34 | 38 |
| 15 | 29 | 40 | 31 | 31 | 34 | 34 |
| 16 | 32 | 21 | 47 | 31 | 20 | 49 |
| 17 | 36 | 30 | 34 | 31 | 27 | 43 |
| 18 | 47 | 24 | 29 | 34 | 27 | 39 |
| 19 | 35 | 24 | 41 | 32 | 27 | 40 |
| 20 | 31 | 31 | 38 | 29 | 27 | 44 |
| 21 | 41 | 19 | 39 | 32 | 24 | 43 |
| 22 | 23 | 40 | 37 | 28 | 35 | 37 |
| 23 | 25 | 35 | 40 | 28 | 31 | 41 |
| 24 | 23 | 38 | 40 | 28 | 32 | 40 |
| 25 | 33 | 26 | 40 | 31 | 26 | 44 |

Figure 17:
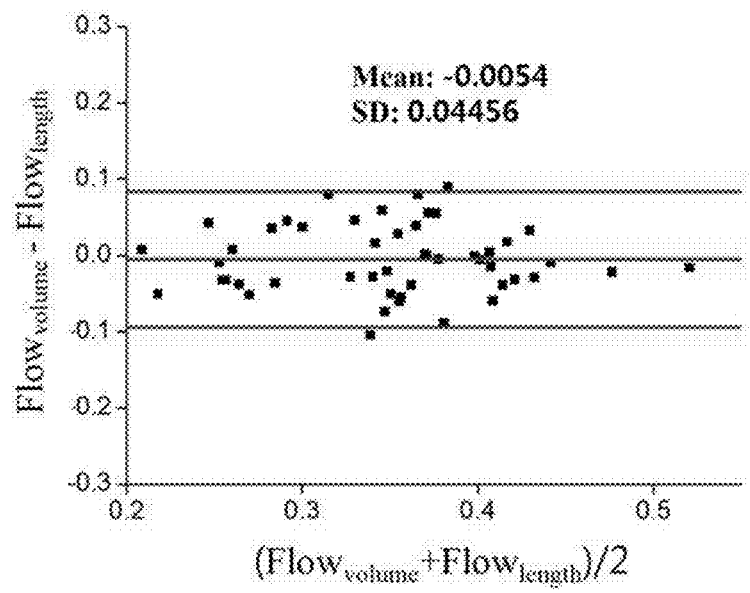
FIG. 17 is a Bland-Altman plot showing a blood flow rate found according to the present invention and a blood flow rate found according to the conventional method.
Figure 18:
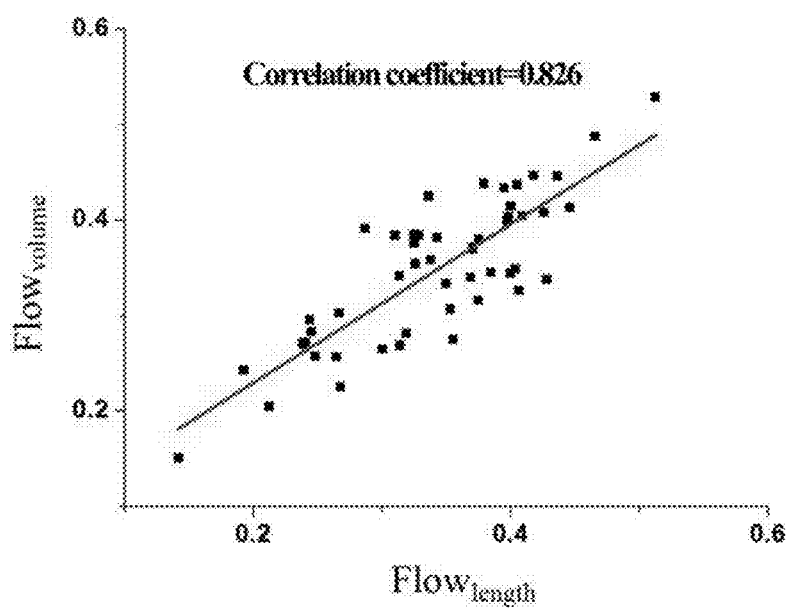
FIG. 18 is a view showing a correlation analysis result for the graph shown in FIG. 17.

The blood flow rates found for the RCA and the LCX are shown in FIG. 17 by the Bland-Altman plot. FIG. 18 shows a correlation analysis result for the Bland-Altman plot shown in FIG. 17. Referring to FIG. 18, it can be noted that the blood flow rate found by the present method and the blood flow rate found by the conventional method have a very high correlation because the correlation coefficient is 0.826. The Bland-Altman plot is a graph for analyzing whether there is a difference between the values found by the two methods. The intermediate line in FIG. 17 indicates a mean value. As the mean value comes close to 0, the difference between the values found by the two methods becomes smaller. As the SD value comes close to 0, the difference between the values found by the two methods becomes similar.

The embodiments described above are nothing more than preferred embodiments of the present invention and are not intended to limit the scope of the present invention. Those skilled in the art may make different changes, modifications or substitutions without departing from the spirit and scope of the present invention. It is to be understood that such changes, modifications or substitutions fall within the scope of the present invention.

What is claimed is:

1. A method for determining cardiovascular information using a computer system, the method comprising the steps of:

receiving image data including a plurality of coronary arteries originating from an aorta;

processing the image data to generate three-dimensional shape models of the coronary arteries;

simulating a blood flow for the generated three-dimensional shape models of the coronary arteries; and determining a fractional flow reserve (FFR) of the coronary arteries based on a blood flow simulation result, wherein, in the step of simulating the blood flow, a computational fluid dynamics model is applied to the three-dimensional shape models of the coronary arteries, a lumped parameter model is combined with the computational fluid dynamics model, and a simplified coronary artery circulation model including the coronary arteries, capillaries of the coronary arteries and coronary veins is used as the lumped parameter model, wherein the step of simulating the blood flow includes a step of finding lengths of centerlines of the three-dimensional shape models of the coronary arteries, resistance values of the capillaries of the coronary arteries are set based on a ratio of blood flow rates in the coronary arteries when combining the simplified coronary artery circulation model with the computational fluid dynamics model, and the ratio of the blood flow rates in the coronary arteries is set based on a ratio of the lengths of the centerlines of the three-dimensional shape models of the coronary arteries, and wherein the ratio of the blood flow rates in the coronary arteries is determined by the following mathematical formula:

$$Q_{LAD}:Q_{LCX}:Q_{RCA} = l_{LAD}:l_{LCX}:\frac{1}{\frac{\alpha}{(l_{RCA})_{RV}} + \frac{1}{(l_{RCA})_{LV}}},$$

where $Q_{LAD}$ is a blood flow rate of a left anterior descending coronary artery, $l_{LAD}$ is a length of the left anterior descending coronary artery, $Q_{LCX}$ is a blood flow rate of a left circumflex coronary artery, $l_{LCX}$ is a length of the left circumflex coronary artery, $Q_{RCA}$ is a blood flow rate of a right coronary artery, $l_{RCA}$ is a length of the right coronary artery, $(l_{RCA})_{RV}$ is a length of a portion of the right coronary artery for supplying blood to a right ventricle, is a length of a portion of the right coronary artery for supplying blood to a left ventricle, and $\alpha$ is a correction coefficient of a blood vessel for supplying blood to the right ventricle.

2. The method of claim 1, wherein in the step of simulating the blood flow, when applying the computational fluid dynamics model to the three-dimensional shape models of the coronary arteries, an aorta blood pressure pattern is used as an inlet boundary condition.

3. The method of claim 1, wherein the step of finding the lengths of the centerlines includes:

a step of finding a centerline of a three-dimensional shape model of each of the coronary arteries;

a step of finding a distal end point where a cross-sectional area of the three-dimensional shape model of each of the coronary arteries is equal to or smaller than a predetermined value; and a step of finding a length of the centerline from a branched point where each of the coronary arteries is branched from the aorta, to a distal end point thereof.

4. A method for determining blood vessel information of a patient using a computer system, comprising the steps of:

receiving image data including at least a part of blood vessels originating from an aorta;

processing the received image data to generate three-dimensional models of the blood vessels;

finding a length of each of the blood vessels from a branched point to a distal end in a three-dimensional model of each of the blood vessels; and determining a ratio of blood flow rates in the blood vessels depending on a ratio of the lengths of the blood vessels, wherein the blood vessels include a right coronary artery (RCA), a left anterior descending coronary artery (LAD) and a left circumflex coronary artery (LCX), and in the step of determining the ratio of the blood flow rates, the ratio of the blood flow rates in the blood vessels is determined by the following mathematical formula:

$$Q_{LAD}:Q_{LCX}:Q_{RCA} = l_{LAD}:l_{LCX}:\frac{1}{\frac{\alpha}{(l_{RCA})_{RV}} + \frac{1}{(l_{RCA})_{LV}}},$$

where $Q_{LAD}$ is a blood flow rate of a left anterior descending coronary artery, $l_{LAD}$ is a length of the left anterior descending coronary artery, $Q_{LCX}$ is a blood flow rate of a left circumflex coronary artery, $l_{LCX}$ is a length of the left circumflex coronary artery, $Q_{RCA}$ is a blood flow rate of a right coronary artery, $l_{RCA}$ is a length of the right coronary artery, $(l_{RCA})RV$ is a length of a portion of the right coronary artery for supplying blood to a right ventricle, $(l_{RCA})_{LV}$ is a length of a portion of the right coronary artery for supplying blood to a left ventricle, and $\alpha$ is a correction coefficient of a blood vessel for supplying blood to the right ventricle.

5. The method of claim 4, wherein the step of finding the length of each of the blood vessels includes:

a step of finding a centerline of the three-dimensional model of each of the blood vessels;

a step of finding a distal end point where a cross-sectional area of the three-dimensional model of each of the blood vessels is equal to or smaller than a predetermined value; and a step of finding a length of the centerline from the branched point of each of the blood vessels to a distal end point thereof.

* * * * *